United States Patent

Leppard et al.

[11] Patent Number: 5,534,559
[45] Date of Patent: Jul. 9, 1996

[54] DAYLIGHT CURING COMPOSITIONS CONTAINING BISACYLPHOSPHINE OXIDE PHOTOINITIATORS

[75] Inventors: David G. Leppard, Marly, Switzerland; Manfred Köhler, Freiburg, Germany; Ljubomir Misev, Allschwil, Switzerland

[73] Assignee: Ciba-Geigy Corporation, Tarrytown, N.Y.

[21] Appl. No.: 451,115

[22] Filed: May 25, 1995

Related U.S. Application Data

[63] Continuation of Ser. No. 212,524, Mar. 11, 1994, abandoned.

[30] Foreign Application Priority Data

Mar. 18, 1993 [CH] Switzerland ............... 816/93

[51] Int. Cl.$^6$ ............... C08F 2/50; C08F 4/00; C08L 67/06; C08K 3/22
[52] U.S. Cl. ............... 522/64; 522/28; 522/84; 522/81; 522/107; 522/182; 568/15
[58] Field of Search ............... 522/64, 28, 81, 522/84, 107, 182; 568/15

[56] References Cited

U.S. PATENT DOCUMENTS

| | | | |
|---|---|---|---|
| 4,737,593 | 4/1988 | Ellrich et al. | 568/15 |
| 4,792,632 | 12/1988 | Ellrich et al. | 568/15 |
| 5,218,009 | 6/1993 | Rutsch et al. | 522/16 |

FOREIGN PATENT DOCUMENTS

| | | |
|---|---|---|
| 0160723 | 11/1985 | European Pat. Off. . |
| 0184095 | 6/1986 | European Pat. Off. . |
| 4231579 | 3/1993 | Germany . |
| 04239508 | 8/1992 | Japan . |
| 2259704 | 3/1993 | United Kingdom . |

OTHER PUBLICATIONS

Research Disclosure, (1993) No. 350, Emsworth, GB.
Derwent Abstract 85–284454/46.

*Primary Examiner*—Susan W. Berman
*Attorney, Agent, or Firm*—William A. Teoli, Jr.

[57] ABSTRACT

Ethylenically unsaturated polymerisable compounds can be cured with daylight or with light sources equivalent to daylight by using as hardener a photoinitiator of formula I $$R_1-\overset{O}{\underset{\|}{P}}-\left(\overset{O}{\underset{\|}{C}}-\begin{array}{c}R_2\\ \diagup\hspace{-2pt}\diagdown\\ R_3\hspace{10pt}R_5\end{array}-R_4\right)_2, \quad (I)$$

wherein
  $R_1$ is $C_1$–$C_{12}$alkyl, cyclopentyl, cyclohexyl, unsubstituted phenyl, naphthyl or biphenyl,
  $R_2$ and $R_3$ are each independently of the other $C_1$–$C_{12}$alkyl,
  $R_4$ is hydrogen or $C_1$–$C_{12}$alkyl, and
  $R_5$ is hydrogen or methyl.

19 Claims, No Drawings

DAYLIGHT CURING COMPOSITIONS CONTAINING BISACYLPHOSPHINE OXIDE PHOTOINITIATORS

This application is a continuation of application Ser. No. 08/212,524, filed Mar. 11, 1994, now abandoned.

The present invention relates to a process for curing ethylenically unsaturated polymerisable compounds with daylight or with light sources equivalent to daylight, and to the use of compositions which are curable with daylight or with light sources equivalent to daylight for coating surfaces.

Mono- and bisacylphosphine oxides are known photoinitiators. U.S. Pat. Nos. 4,792,632 and 4,737,593 disclose bisacylphosphine oxides that are used as photocuring agents for dental compositions. Further mono- and bisacylphosphine oxide photoinitiators are disclosed in U.S. Pat. No. 5 218 009. Alkyl bisacylphosphine oxide are disclosed in GB-A-2 259 704. Daylight curable formulations are disclosed in EP-A-160 723. These formulations contain as photocuring agent monoacylphosphine oxides or liquid combinations of these compounds with an β-hydroxyacetophenone, a benzil dialkyl ketal and/or methyl thioxanthone.

For the extensive utility range of photoinitiators there is a host of different effective compounds that are suitable in particular for radiation curing with high-intensity UV lamps. There is, however, also a need for adequately curing polymerisable compositions with daylight or with light sources equivalent to daylight, the intensity of which sources is, per irradiated area, lower than that of the aforementioned UV lamps.

Surprisingly, it has now been found that the cure of polymerisable compositions can be carried out especially well using specific bisacylphosphine oxide photoinitiators.

Accordingly, the invention relates to a process for curing ethylenically unsaturated polymerisable compounds, which comprises adding to said compounds at least one photoinitiator of formula I

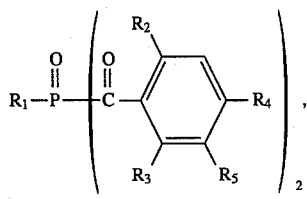

wherein
$R_1$ is $C_1$–$C_{12}$alkyl, cyclopentyl, cyclohexyl, unsubstituted phenyl, naphthyl or biphenyl, or phenyl, naphthyl or biphenyl which are substituted by $C_1$–$C_{12}$alkyl and/or halogen,
$R_2$ and $R_3$ are each independently of the other $C_1$–$C_{12}$alkyl,
$R_4$ is hydrogen or $C_1$–$C_{12}$alkyl, and
$R_5$ is hydrogen or methyl,
and irradiating the mixture so obtained with daylight or with light sources equivalent to daylight.

$R_1$ defined as $C_1$–$C_{12}$alkyl may be linear or branched alkyl and is typically methyl, ethyl, isopropyl, n-propyl, n-butyl, 1-methyl-prop-1-yl, 2-methyl-prop-1-yl, tert-butyl, pentyl, hexyl, heptyl, octyl, 2,4,4-trimethyl-pent-1-yl, 2-ethylhexyl, nonyl, decyl or dodecyl. $R_1$ is typically $C_3$–$C_{10}$alkyl, more particularly $C_3$–$C_8$alkyl, preferably isobutyl.

$R_2$, $R_3$ and $R_4$ defined as $C_1$–$C_{12}$alkyl are typically methyl, ethyl, n-propyl, isopropyl, n-butyl, 1-methyl-prop-1-yl, 2-methyl-prop-1-yl, tert-butyl, pentyl, hexyl, heptyl, octyl, 2,4,4-trimethyl-pent-1-yl, 2-ethylhexyl, nonyl, decyl or dodecyl, preferably $C_1$–$C_4$alkyl, most preferably methyl.

$R_1$ defined as substituted phenyl, naphthyl or biphenyl is mono- or disubstituted, preferably disubstituted, in the aromatic nucleus.

$C_1$–$C_{12}$Alkyl substituents at the phenyl, naphthyl or biphenyl ring may be linear or branched and are typically methyl, ethyl, isopropyl, n-propyl, n-butyl, pentyl, hexyl, heptyl, octyl, nonyl, decyl or dodecyl. The preferred substituent at the phenyl ring is $C_1$–$C_8$alkyl, preferably $C_1$–$C_4$alkyl, most preferably methyl. The alkyl substitution at the phenyl ring is typically in 2,4,6-, 2-, 3- ,4- or 2,5-position. Positions 2, 3, 4 and 2,5 are preferred and position 2,5 is most preferred.

$R_1$ defined as alkyl-substituted phenyl is preferably 2-methylphenyl, 3-methylphenyl, 4-methylphenyl or 2,5-dimethylphenyl. The most preferred meaning is 2,5-dimethylphenyl.

Halogen is fluoro, chloro, bromo or iodo. Chloro is preferred.

$R_5$ is preferably hydrogen.

A preferred process is one wherein $R_1$ in the compounds of formula I is $C_2$–$C_{10}$alkyl, cyclopentyl, cyclohexyl or phenyl which is unsubstituted or substituted by $C_1$–$C_4$alkyl, Cl and/or Br.

An interesting process is also that wherein $R_1$ in the compounds of formula I is $C_3$–$C_8$alkyl, cyclopentyl, cyclohexyl or phenyl which is unsubstituted or substituted in 2-, 3-, 4- or 2,5-position by $C_1$–$C_4$alkyl.

A particularly preferred process is that wherein $R_1$ in the compounds of formula I is $C_4$–$C_{12}$alkyl, cyclopentyl or cyclohexyl, $R_2$ and $R_3$ are each independently of the other $C_1$–$C_{12}$alkyl and $R_4$ is hydrogen or $C_1$–$C_{12}$alkyl.

A preferred process is that wherein $R_2$ and $R_3$ in the compounds of formula I are $C_1$–$C_4$alkyl and $R_4$ is hydrogen or $C_1$–$C_4$alkyl.

A particularly preferred process is that wherein $R_2$ and $R_3$ in the compounds of formula I are methyl and $R_4$ is hydrogen or methyl.

A further interesting process is that wherein $R_2$, $R_3$ and $R_4$ in the compounds of formula I are methyl.

A further preferred process is that wherein $R_2$, $R_3$ and $R_4$ in the compounds of formula I are methyl and $R_5$ is hydrogen.

A process meriting special mention is that wherein $R_1$ in the compounds of formula I is $C_3$–$C_8$alkyl.

A particularly preferred process is that wherein $R_1$ in the compounds of formula I is isobutyl.

A very particularly preferred process is that wherein $R_1$ in the compounds of formula I is phenyl.

The compounds of formula I may conveniently be prepared by diacylating a primary phosphine III with at least 2 equivalents of an acid chloride II in the presence of at least 2 equivalents of a base, and subsequent oxidation of the resultant diacylphosphine IV to give the phosphine oxide, in accordance with the following scheme:

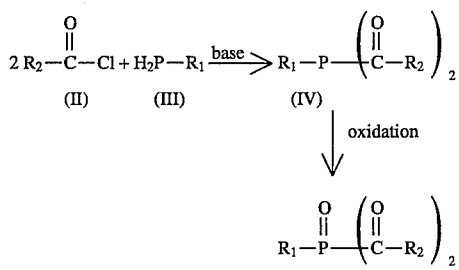

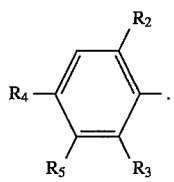

A is a radical $R_1$, $R_2$, $R_3$, $R_4$ and $R_5$ have the meanings given above.

Illustrative examples of suitable bases are tertiary amines, alkali metals, lithium diisopropylamide, alkali metal alkoxides or alkali metal hydrides. The first reaction step is preferably carried out in solution. Suitable solvents are in particular hydrocarbons, including alkanes, benzene, toluene or xylene. After separation of the resultant base chloride, the phosphine (IV) can be isolated by evaporation or the second reaction step is carried out with the solution of the crude product without isolation of (IV). Particularly suitable oxidants for the second step are hydrogen peroxide and organic peroxy compounds, typically peracetic acid, or air.

The starting primary phosphines (III) are known compounds some of which are commercially available, or they can be prepared by methods analogous to those employed for obtaining known compounds (q.v. Houben-Weyl, Methoden der Org. Chemie [Methods of Organic Chemistry], XII/1, 60–63 (1963), G. Thieme-Verlag, Stuttgart). The acid chlorides of formula (II) or (IIa) are also prepared by known prior art methods.

Illustrative examples of photoinitiators of formula I useful in the daylight curable compositions are:

bis(2,4,6-trimethylbenzoyl)methylphosphine oxide
bis(2,4,6-trimethylbenzoyl)ethylphosphine oxide
bis(2,4,6-trimethylbenzoyl)-isopropylphosphine oxide
bis(2,4,6-trimethylbenzoyl)-n-propylphosphine oxide
bis(2,4,6-trimethylbenzoyl)-n-butylphosphine oxide
bis(2,4,6-trimethylbenzoyl)-tert-butylphosphine oxide
bis(2,4,6-trimethylbenzoyl)-(2-methyl-prop-1-yl)phosphine oxide
bis(2,4,6-trimethylbenzoyl)-(1-methyl-prop-1-yl)phosphine oxide
bis(2,4,6-trimethylbenzoyl)-cyclohexylphosphine oxide
bis(2,4,6-trimethylbenzoyl)-n-pentylphosphine oxide
bis(2,4,6-trimethylbenzoyl)-n-hexylphosphine oxide
bis(2,4,6-trimethylbenzoyl)-(2-ethyl-hex-1-yl)phosphine oxide
bis(2,4,6-trimethylbenzoyl)-n-octylphosphine oxide
bis(2,4,6-trimethylbenzoyl)-(2,4,4-trimethyl-pent-1-yl)phosphine oxide
bis(2,4,6-trimethylbenzoyl)-n-decylphosphine oxide
bis(2,4,6-trimethylbenzoyl)-phenylphosphine oxide
bis(2,4,6-trimethylbenzoyl)-(4-methylphenyl)phosphine oxide
bis(2,6-dimethylbenzoyl)-methylphosphine oxide
bis(2,6-dimethylbenzoyl)-ethylphosphine oxide
bis(2,6-dimethylbenzoyl)-i-propylphosphine oxide
bis(2,6-dimethylbenzoyl)-n-propylphosphine oxide
bis(2,6-dimethylbenzoyl)-(2,4,4-trimethyl-pent-1-yl)phosphine oxide
bis(2,6-dimethylbenzoyl)-(2-methyl-prop-1-yl)phosphine oxide
bis(2,6-dimethylbenzoyl)-n-butylphosphine oxide
bis(2,6-dimethylbenzoyl)-t-butylphosphine oxide
bis(2,6-dimethylbenzoyl)-(1-methyl-prop-1-yl)phosphine oxide
bis(2,6-dimethylbenzoyl)-cyclohexylphosphine oxide
bis(2,6-dimethylbenzoyl)-n-pentylphosphine oxide
bis(2,6-dimethylbenzoyl)-n-hexylphosphine oxide
bis(2,6-dimethylbenzoyl)-(2-ethyl-hex-1-yl)phosphine oxide
bis(2,6-dimethylbenzoyl)-n-octylphosphine oxide
bis(2,6-dimethylbenzoyl)-(2,4,4-trimethyl-pent-1-yl)phosphine oxide
bis(2,6-dimethylbenzoyl)-phenylphosphine oxide
bis(2,6-dimethylbenzoyl)-(2,5-dimethylphenyl)phosphine oxide
bis(2,6-dimethylbenzoyl)-n-octylphosphine oxide
bis(2,4,6-triethylbenzoyl)-methylphosphine oxide
bis(2,4,6-triethylbenzoyl)-ethylphosphine oxide
bis(2,4,6-triethylbenzoyl)-i-propylphosphine oxide
bis(2,4,6-triethylbenzoyl)-n-propylphosphine oxide
bis(2,4,6-triethylbenzoyl)-n-butylphosphine oxide
bis(2,4,6-triethylbenzoyl)-t-butylphosphine oxide
bis(2,4,6-triethylbenzoyl)-(2-methyl-prop-1-yl)phosphine oxide
bis(2,4,6-triethylbenzoyl)-(1-methyl-prop-1-yl)phosphine oxide
bis(2,4,6-triethylbenzoyl)-cyclohexylphosphine oxide
bis(2,4,6-triethylbenzoyl)-n-pentylphosphine oxide
bis(2,4,6-triethylbenzoyl)-n-hexylphosphine oxide
bis(2,4,6-triethylbenzoyl)-(2-ethyl-hex-1-yl)phosphine oxide
bis(2,4,6-triethylbenzoyl)-n-octylphosphine oxide
bis(2,4,6-triethylbenzoyl)-(2,4,4-trimethyl-pent-1-yl)phosphine oxide
bis(2,4,6-triethylbenzoyl)-n-decylphosphine oxide
bis(2,4,6-triethylbenzoyl)-phenylphosphine oxide
bis(2,6-diethylbenzoyl)-(2,4,4-trimethyl-pent-1-yl)phosphine oxide
bis(2,6-diethylbenzoyl)-(2-methyl-prop-1-yl)phosphine oxide
bis(2,6-diethylbenzoyl)-n-butylphosphine oxide
bis(2,6-diethylbenzoyl)-t-butylphosphine oxide
bis(2,6-diethylbenzoyl)-(1-methyl-prop-1-yl)phosphine oxide
bis(2,6-diethylbenzoyl)-cyclohexylphosphine oxide
bis(2,6-diethylbenzoyl)-n-pentylphosphine oxide
bis(2,6-diethylbenzoyl)-n-hexylphosphine oxide
bis(2,6-diethylbenzoyl)-(2-ethyl-hex-1-yl)phosphine oxide
bis(2,6-diethylbenzoyl)-n-octylphosphine oxide
bis(2,6-diethylbenzoyl)-phenylphosphine oxide bis(2,4,6-triisopropylbenzoyl)-n-butylphosphine oxide
bis(2,4,6-triisopropylbenzoyl)-t-butylphosphine oxide
bis(2,4,6-triisopropylbenzoyl)-(2-methyl-prop-1-yl)phosphine oxide
bis(2,4,6-triisopropylbenzoyl)-(1-methyl-prop-1-yl)phosphine oxide
bis(2,4,6-triisopropylbenzoyl)-cyclohexylphosphine oxide
bis(2,4,6-triisopropylbenzoyl)-n-pentylphosphine oxide
bis(2,4,6-triisopropylbenzoyl)-n-hexylphosphine oxide
bis(2,4,6-triisopropylbenzoyl)-(2-ethyl-hex-1-yl)-phosphine oxide
bis(2,4,6-triisopropylbenzoyl)-n-octylphosphine oxide
bis(2,4,6-triisopropylbenzoyl)-(2,4,4-trimethyl-pent-1-yl)-phosphine oxide
bis(2,4,6-triisopropylbenzoyl)-n-decylphosphine oxide
bis(2,4,6-triisopropylbenzoyl)-phenylphosphine oxide
bis(2,4,6-tri-n-butylbenzoyl)-(2-methyl-prop-1-yl)-phosphine oxide
bis(2,4,6-tri-n-butylbenzoyl)-(2,4,4-trimethyl-pent-1-yl)-phosphine oxide
bis(2,4,6-tri-n-propylbenzoyl)-(2-methyl-prop-1-yl)phosphine oxide
bis(2,4,6-tri-n-propylbenzoyl)-n-butylphosphine oxide
bis(2,4,6-tri-(1-methyl-prop-1-yl)benzoyl)-n-octylphosphine oxide
bis(2,4,6-tri-(1-methyl-prop-1-yl)benzoyl)-n-butylphosphine oxide
bis(2,4,6-tri-(2-methyl-prop-1-yl)benzoyl)-(2,4,4-trimethyl-pent-1-yl)phosphine oxide
bis(2,4,6-tri-(2-methyl-prop-1-yl)benzoyl)-(2-methyl-prop-1-yl)phosphine oxide
bis(2,4,6-tri-t-butylbenzoyl)-n-butylphosphine oxide
bis(2,6-dimethyl-4-n-butyl-benzoyl)-(2-methyl-prop-1-yl)phosphine oxide
bis(2,6-dimethyl-4-n-butyl-benzoyl)-phenylphosphine oxide
bis(2,4,6-trimethyl-benzoyl)-(2,5-dimethylphenyl)phosphine oxide
bis(2,6-dimethyl-4-n-butyl-benzoyl)-(2,5-dimethylphenyl)phosphine oxide The ethylenically unsaturated polymerisable compounds can contain one or more than one olefinic double bond. They may be low molecular (monomeric) or high molecular (oligomeric) compounds.

Typical examples of monomers containing one double bond are alkyl or hydroxyalkyl acrylates or methacrylates, for example methyl, ethyl, butyl, 2-ethylhexyl and 2-hydroxyethyl acrylate, isobornyl acrylate, and methyl and ethyl methacrylate. Further examples of these monomers are acrylonitrile, acrylamide, methacrylamide, N-substituted (meth)acrylamides, vinyl esters such as vinyl acetate, vinyl ethers such as isobutyl vinyl ether, styrene, alkylstyrenes, halostyrenes, N-vinylpyrrolidone, vinyl chloride and vinylidene chloride.

Examples of monomers containing more than one double bond are ethylene glycol diacrylate, propylene glycol diacrylate, neopentyl glycol diacrylate, hexamethylene glycol diacrylate, bisphenol A diacrylate, 4,4'-bis(2-acryloyloxyethoxy)diphenylpropane, trimethylolpropane triacrylate, pentaerythritol triacrylate and tetraacrylate, pentaerythritol divinyl ether, vinyl acrylate, divinyl benzene, divinyl succinate, diallyl phthalate, triallyl phosphate, triallyl isocyanurate or tris(2-acryloylethyl)isocyanurate. Examples of high molecular weight (oligomeric) polyunsaturated compounds are acrylated epoxy resins, acrylated polyethers, acrylated polyurethanes and acrylated polyesters. Further examples of unsaturated oligomers are unsaturated polyester resins, which are usually prepared from maleic acid, phthalic acid and one or more diols and which have molecular weights of from about 500 to 3000. Unsaturated oligomers of this type are also known as prepolymers.

Typical examples of unsaturated compounds are esters of ethylenically unsaturated carboxylic acids and polyols or polyepoxides, and polymers containing ethylenically unsaturated groups in the chain or in side groups, including unsaturated polyesters, polyamides and polyurethanes and copolymers thereof, polybutadiene and butadiene copolymers, polyisoprene and isoprene copolymers, polymers and copolymers containing (meth)acrylic groups in side-chains, as well as mixtures of one or more than one such polymer.

Illustrative examples of unsaturated carboxylic acids are acrylic acid, methacrylic acid, crotonic acid, itaconic acid, cinnamic acid, unsaturated fatty acids such as linolenic acid or oleic acid. Acrylic and methacrylic acid are preferred.

Suitable polyols are aromatic and, preferably, aliphatic and cycloaliphatic polyols. Aromatic polyols are typically hydroquinone, 4,4'-dihydroxydiphenyl, 2,2-bis(4-hydroxyphenyl)propane, as well as novolaks and resols. Polyepoxides include those based on the cited polyols, preferably on the aromatic polyols and epichlorohydrin. Further suitable polyols are polymers and copolymers which contain hydroxyl groups in the polymer chain or in side groups, for example polyvinyl alcohol and copolymers thereof or hydroxyalkyl polymethacrylates or copolymers thereof. Other suitable polyols are oligoesters carrying hydroxyl end groups.

Illustrative examples of aliphatic and cycloaliphatic polyols are alkylenediols containing preferably 2 to 12 carbon atoms, including ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably 200 to 1500, 1,3-cyclopentanediol, 1,2-, 1,3-or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be esterified partially or completely with one or with different unsaturated carboxylic acids, in which case the free hydroxyl groups of the partial esters may be modified, for example etherified, or esterified with other carboxylic acids.

Illustrative examples of esters are: trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentacrylate, dipentaerythritol hexacrylate, tripentaerythritol octacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentacrylate, sorbitol hexacrylate, oligoester acrylates and methacrylates, glycerol di- and-triacrylate, 1,4-cyclohexanediacrylate, bisacrylates and bismethacrylates of polyethylene glycol having molecular weights of 200 to 1500, or mixtures thereof.

Suitable ethylenically unsaturated polymerisable compounds are also the amides of identical or different unsaturated carboxylic acids of aromatic, cycloaliphatic and aliphatic polyamines containing preferably 2 to 6, more particularly 2 to 4, amino groups. Exemplary of such polyamines are ethylenediamine, 1,2- or 1,3-propylenediamine, 1,2-, 1,3-or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, bis(βaminoethyl) ether, diethylenetriamine, triethylenetetramine, bis(β-aminoethoxy)ethane or bis(β-aminopropoxy)ethane. Other suitable polyamines are polymers and copolymers which may contain additional amino groups in the side-chain and oligoamides containing amino end groups. Exemplary of such unsaturated amides are: methylenebisacrylamide, 1,6-hexamethylenebisacrylamide, diethylenetriaminetrismethacrylamide, bis(methacrylamidopropoxy)ethane, β-methacrylamidoethylmethacrylate, N-[(β-hydroxyethoxy-)ethyl]acrylamide.

Suitable unsaturated polyesters and polyamides are derived typically from maleic acid and diols or diamines. Maleic acid can be partially replaced by other dicarboxylic acids such as fumaric acid, itaconic acid, citraconic acid, mesaconic acid or chloromaleic acid. To control the reactivity of the polyester and to influence the crosslinking density and hence the product properties, it is possible to use in addition to the unsaturated dicarboxylic acids different amounts of saturated dicarboxylic acids such as phthalic acid, isophthalic acid, terephthalic acid, tetrahydrophthalic acid, succinic acid or adipic acid. The unsaturated polyesters can be used together with ethylenically unsaturated comonomers such as styrene. The polyesters and polyamides can also be derived from dicarboxylic acids and ethylenically unsaturated diols or diamines, especially from those with long chains containing typically from 6 to 20 carbon atoms. Polyurethanes are typically those derived from saturated or unsaturated diisocyanates and unsaturated and saturated diols.

Suitable polyester acrylates or acrylated polyesters are obtained by reacting oligomers, typically epoxides, urethanes, polyethers or polyesters, with acrylates such as hydroxyethyl acrylate or hydroxypropyl acrylate.

Polybutadiene and polyisoprene and copolymers thereof are known. Suitable comonomers include olefins such as ethylene, propene, butene, hexene, (meth)acrylates, acrylonitrile, styrene or vinyl chloride. Polymers containing (meth)acrylate groups in the side-chain are also known. They may typically be reaction products of epoxy resins based on novolak with (meth)acrylic acid, homo- or copolymers of polyvinyl alcohol or their hydroxyalkyl derivatives which are esterified with (meth)acrylic acid or homo- and copolymers of (meth)acrylates which are esterified with hydroxyalkyl(meth)acrylates.

Preferred monomers are typically alkyl- or hydroxyalkyl acrylates or methacrylates, styrene, ethylene glycol diacrylate, propylene glycol diacrylate, neopentyl glycol diacrylate, hexamethylene glycol diacrylate or bisphenol A diacrylate, 4,4'-bis(2-acryloyloxyethoxy)diphenylpropane, trimethylolpropane triacrylate, pentaerythritol triacrylate or tetraacrylate, preferably acrylates, styrene, hexamethylene glycol or hisphenol A diacrylate, 4,4'-bis(2-acryloyloxyethoxy)diphenylpropane or trimethylolpropane triacrylate.

Particularly preferred (oligomeric) polyunsaturated compounds are polyester acrylates or unsaturated polyester resins which are prepared from maleic acid, fumaric acid, phthalic acid and one or more than one diol, and which have molecular weights from about 500 to 3000.

Preferred unsaturated carboxylic acids are acrylic acid and methacrylic acid.

The photopolymerisable compounds are used by themselves or in any desired mixtures. It is preferred to use mixtures of polyol(meth)acrylates.

Binders may also be added to the unsaturated photopolymerisable compounds. The addition of binders is particularly useful if the photopolymerisable compounds are liquid or viscous substances. The amount of binder may be from 5–95, preferably 10–90 and, most preferably, 40–90, percent by weight, based on the entire composition. The choice of binder will depend on the field of use and the desired properties therefor, such as the ability of the compositions to be developed in aqueous and organic solvent systems, adhesion to substrates and susceptibility to oxygen.

Suitable binders are typically polymers having a molecular weight of about 5000 to 2 000 000, preferably 10 000 to 1 000 000. Illustrative examples are: homo- and copolymers of acrylates and methacrylates, including copolymers of methyl methacrylate/ethyl acrylate/methacrylic acid, poly(alkylmethacrylates), poly(alkylacrylates); cellulose esters and ethers such as cellulose acetate, cellulose acetobutyrate, methyl cellulose, ethyl cellulose; polyvinyl butyral, polyvinyl formal, cyclised rubber, polyethers such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethylene adipamide), polyesters such as poly(ethylene glycol terephthalate) and poly(hexamethylene glycol succinate).

The unsaturated compounds can also be used in admixture with non-photopolymerisable film-forming components. These components may be physically drying polymers or solutions thereof in organic solvents, for example nitrocellulose or cellulose acetobutyrate.

Mixtures of a prepolymer with polyunsaturated monomers which, additionally contain a further unsaturated monomer are frequently used in paint systems. The prepolymer in this instance primarily determines the properties of the paint film and, by varying it, the skilled person can influence the properties of the cured film. The polyunsaturated monomer acts as crosslinking agent that renders the paint film insoluble. The mono-unsaturated monomer acts as reactive diluent with the aid of which the viscosity is lowered without having to use a solvent. Moreover, properties of the cured composition such as curing rate, crosslinking density and surface properties are dependent on the choice of monomer.

Unsaturated polyester resins are usually used in two-component systems, together with a mono-unsaturated monomer, preferably with styrene.

A preferred process is that wherein the ethylenically unsaturated polymerisable compounds are a mixture of (i) at least one oligomeric compound and (ii) at least one monomer.

An interesting process is that wherein the ethylenically unsaturated polymerisable compounds are a mixture of (i)

unsaturated polyesters, especially those that are prepared from maleic acid, fumaric acid and/or phthalic acid and one or more than one diol, and which have molecular weights of 500 to 3000, and (ii) acrylates, methacrylates and/or stryene.

An important process is also that wherein the ethylenically unsaturated polymerisable compounds are a mixture of (i) unsaturated polyesters and (ii) acrylates and/or methacrylates.

Another interesting process is that wherein the ethylenically unsaturated polymerisable compounds are a mixture of (i) unsaturated polyester acrylates and (ii) acrylates and/or methacrylates.

The compounds of formula I can be used as photoinitiators for curing ethylenically unsaturated polymerisable compounds with daylight or with light sources equivalent to daylight. Accordingly, the invention also relates to the use of compounds of formula I for curing ethylenically unsaturated polymerisable compounds with daylight or with light sources equivalent to daylight.

In addition to the photoinitiator, the photopolymerisable compositions may contain different additives. To enhance the dark storage stability it is possible to add copper compounds, including copper naphthenate, copper stearate or copper octoate, phosphorus compounds, including triphenylphosphine, tributylphosphine, triethyl phosphite, triphenyl phosphite, or tribenzyl phosphite, quaternary ammonium compounds, such as tetramethylammonium chloride or trimethylbenzylammonium chloride, or hydroxylamine derivatives, such as N-diethylhydroxylamine. The exclusion of atmospheric oxygen during the polymerisation may be effected by adding paraffin or similar wax-like substances which, at the onset of polymerisation, migrate to the surface owing to lack of solubility in the polymer and form a transparent film which prevents air from entering the system. Minor amounts of UV absorbers, typically those of the benzothiazole, benzophenone, oxanilide or hydroxyphenyl-S-triazine type, may be added as light stabilisers. Better still is the addition of light stabilisers that do not absorb UV light, for example sterically hindered amines (HALS).

The photopolymerisation can be accelerated by adding amines such as triethanolamine, N-methyl-diethanolamine, ethyl p-dimethylaminobenzoate or Michler's ketone. The action of the amines can be intensified by the addition of aromatic ketones of the benzophenone type. Amines useful as oxygen scavengers are typically the substituted N,N-dialkylanilines described in EP-A-339 841.

The photopolymerisation can further be accelerated by the addition of photosensitisers. These photosensitisers are preferably aromatic carbonyl compounds such as benzophenone, thioxanthone, anthraquinone and 3-acylcoumarin derivatives as well as 3-(aroylmethylene)thiazolines, and also eosine, rhodanine and erthrosine dyes. The compositions of this invention may also contain a photoreducible dye such as a xanthene, benzoxanthene, benzothioxanthene, thiazine, pyronine, porphyrine or acridin dye, and/or a trihalomethyl compound which is cleavable by irradiation. Similar compositions are disclosed, inter alia, in EP-A-445 624.

The curing process of, in particular, for example with $TiO_2$, pigmented systems, can be supported by the addition of a component, which produces radicals under thermic conditions as, for example, an azo compound as 2,2'-azobis(4-methoxy-2,4-dimethylvaleronitril) or a peroxy compound such as hydroperoxide or peroxycarbonate, for example t-butylhydroperoxide, as is disclosed, for example, in EP-A 245 639.

Depending on the envisaged end use further customary additives are fluorescent whitening agents, fillers, pigments, dyes, wetting agents or flow control agents.

The invention also relates to a process in which the ethylenically unsaturated polymerisable compounds are dissolved or emulsified in water.

Many varieties of such photocurable aqueous prepolymer dispersions are commercially available. Such dispersions will generally be understood as meaning dispersions comprising water and at least one prepolymer dispersed therein. The concentration of water in these systems is in the range from typically 5 to 80% by weight, preferably from 30 to 60% by weight. The dispersions contain the photocurable prepolymer or mixture thereof in a concentration of 95 to 20% by weight, preferably of 70 to 40 % by weight. The sum of the indicated percentages of water and prepolymers in these compositions is always 100. Depending on the end use, the modifiers and additives are added in varying amounts.

The photocurable film-forming prepolymers which are dispersed, and often dissolved, in water are mono- or polyfunctional, ethylenically unsaturated prepolymers which can be initiated by free radicals and are known per se for use in aqueous prepolymer dispersions. They typically contain from 0.01 to 1.0 mol of polymerisable double bonds per 100 g of prepolymer and also have an average molecular weight of at least 400, preferably of 500 to 10 000. Depending on the envisaged end use, however, prepolymers of higher molecular weight are also suitable, including polyesters having an acid number of not more than 10 and containing polymerisable C—C double bonds, polyethers containing polymerisable C—C double bonds, hydroxyl group containing reaction products of a polyepoxide containing at least two epoxy groups per molecule with at least one $\alpha,\beta$-ethylenically unsaturated carboxylic acid, polyurethane(meth)acrylates as well as the acrylic copolymers containing $\alpha,\beta$-ethylenically unsaturated acrylic radicals described in EP-A-12 339. It is also possible to use mixtures of these prepolymers. Also suitable are the polymerisable prepolymers disclosed in EP-A-33 896 which are thioether polyadducts of polymerisable prepolymers having an average molecular weight of at least 600, a carboxyl group value of 0.2 to 15%, and containing 0.01 to 0.8 mol of polymerisable C—C double bonds per 100 g of prepolymer. Other suitable aqueous dispersions based on special alkyl (meth)acrylate polymers are disclosed in EP-A-41 125. Suitable water-dispersible photocurable prepolymers of urethane acrylates are disclosed in DE-A-29 36 039.

As further additives these photocurable aqueous prepolymer dispersions may contain dispersants, emulsifiers, antioxidants, light stabilisers, dyes, pigments, fillers such as talcum, gypsum, rutile, carbon black, zinc oxide, iron oxides, reaction accelerators, flow control agents, lubricants, wetting agents, thickeners, dulling agents, antifoams and other modifiers conventionally used in coating technology. Suitable dispersants are water-soluble high molecular weight organic compounds carrying polar groups, typically polyvinyl alcohols, polyvinyl pyrrolidone or cellulose ethers. Suitable emulsifiers may be nonionic emulsifiers and, in some cases, ionic emulsifiers may also be used.

When using ethylenically unsaturated polymerisable compounds in aqueous systems or emulsions, the amount of water is expediently removed before the cure, conveniently by evaporation.

The photopolymerisable compositions contain the photoinitiator conveniently in an amount of 0.05 to 15% by weight, preferably 0.2 to 5% by weight, based on the composition.

A process is therefore preferred in which the photoinitiator is used in an amount of 0.05 to 15% by weight, preferably from 0.2 to 5% by weight.

In specific cases it may be advantageous to use mixtures of two or more photoinitiators of this invention. Mixtures with known photoinitiators may of course also be used, typically mixtures with benzophenones, acetophenone derivatives, such as α-hydroxyalkylphenylketones, 1-benzoyl-1-hydroxy-1-methylethane, dialkoxyacetophenones, α-hydroxy- or α-aminoacetophenones, e.g. 4-morpholinophenyl-2-benzyl-2-dimethylamino-propionyl, 4-aroyl-1,3-dioxolanes, benzoin alkyl ethers and benzil ketals, or monoacylphosphine oxides, further bisacylphosphine oxides or diisopropylxanthogen disulfide.

Accordingly, the invention also relates to a process comprising the use of other photoinitiators and/or additives in addition to the photoinitiator of formula I The invention also relates to compositions comprising (A) at least one ethylenically unsaturated polymerisable compound, and (B) at least one photoinitiatior of formula I, which compositions are curable by irradiation with daylight or with light sources equivalent to daylight.

The daylight curable photopolymerisable compositions can be used for a variety of utilities, typically as clear coating formulations, white enamel formulations for wood or metal, as coating materials for paper, wood or plastics, as coating materials for exterior coatings and road markings.

The daylight curable photocurable compositions of this invention may suitably be used as coating compositions for substrates of all kinds, such as wood, paper, ceramics, synthetic resins such as polyesters, polyethylene terephthalate, polyolefins or cellulose acetate. Further utilities are metal coating, for example for painting metal constructions such as bridges, or wood constructions as in lightweight constructions, and for fabricating composites.

The novel process for curing with daylight or with light sources equivalent to daylight is also particularly suitable for curing moulded objects made from composites. The composite consists of a serf-supporting matrix material, typically a glass fibre fabric that is impregnated with the light curable formulation. When the formulation is exposed to daylight, a precure is initially effected. In this state the material is no longer flowable, substantially tack-free and mouldable. To effect the full cure, the moulded object is exposed again to daylight. In this manner superior mechanical stability and resistance are imparted to moulded objects made from composites.

The invention also relates to a process for coating surfaces by applying a formulation as described above to said surfaces and curing the layer by irradiation with daylight or a light source equivalent to daylight.

The substrate surface can be coated by applying to said substrate a liquid composition or suspension. The choice of solvent and the concentration will depend mainly on the type of formulation and on the coating method employed. The suspension is uniformly applied to a substrate by known coating techniques such as by knife coating, brushing or spraying. The add-on (layer thickness) of the novel compositions on the surface of the respective substrate will depend on the desired field of application. The layer thicknesses are generally in the range from c. 50 μm to 7 mm, e.g. from 250 μm to 5 mm, preferably from 500 μm to 2 mm.

The cure of the compositions is effected by irradiation with daylight or with light sources equivalent to daylight. By daylight or with light sources equivalent to daylight will be understood as meaning radiation in the wavelength from 350–500 nm. To effect the cure the radiation must be in the wavelength range from 350–450 nm. In contrast to standard UV curing with radiation of high intensity, in the process of this invention the cure is effected with radiation of low intensity over an extended period of time. Such radiation is typically daylight (sunlight), as well as radiation sources equivalent to daylight. Daylight (sunlight) differs from the radiation of the artificial light sources conventionally used in UV curing with respect to its spectral make-up and the intensity. The absorption characteristics and the radical-forming properties of the bisacylphosphine oxides used in the process of this invention are suited in particular manner to utilise sunlight as natural light source for the cure.

The photoinitiators hitherto used in UV curing methods, typically benzil dimethyl ketal, α-hydroxy- or α-aminoketones, are unable to cure the surface of a film with daylight in a satisfactory manner. The selected bisacylphosphine oxides used in the process of his invention produce within 1–120, e.g. 1–60, 1–30 and, preferably, 1–15, minutes, tack-free surfaces upon exposure to daylight or to sources equivalent to daylight. The intensities of the light sources useful for the cure are in the range from 10 to 30, preferably from 10 to 20 mW/cm$^2$. By way of contrast, the intensities of the artificial light sources conventionally used for UV curing are greater than 50 mW/cm$^2$ in the UV range.

By artificial light sources equivalent to daylight as used in the process of this invention are meant lamps of low intensity such as specific fluorescent lamps, e.g. the Philips TL05 or TL09 special fluorescent lamp.

The film to be cured can be exposed direct to sunlight or light sources equivalent to daylight. The cure can, however, also be effected behind a transparent layer (e.g. a pane of glass or plastic shet).

Complicated and expensive apparatus is superfluous when using light sources that emit light of low intensity, and the compositions can be used in particular for special exterior applications. The cure with daylight or with light sources equivalent to daylight is an alternative to the standard moving belt method of UV curing. In contrast to the moving belt method, which is particularly suitable for flat parts, the daylight cure can be used for exterior coatings on stationary and fixed objects or constructions. These are typically coatings on buildings, facades, bridges, ships or markings on roads and sites as disclosed, inter alia, in EP-A-160 723.

The cure with daylight or with light sources equivalent to daylight is an energy-saving method and, in exterior applications, no emission of volatile organic components into the environment occurs.

Wipe-resistant surfaces are achieved with the process of this invention using daylight or light sources equivalent to daylight over 1–120 minutes, e.g. 1–60 minutes, preferably 1–30 minutes, most preferably 1–15 minutes.

The cure with daylight or light sources equivalent to daylight is, however, also suitable for series curing in which the objects are so positioned that angular areas are also exposed to daylight. In this connection, minors or reflectors can also be used.

The use of effective photoinitiators is necessary for the cure in an acceptable period of time with daylight or light sources equivalent to daylight whose intensity/unit of area is lower than that of UV lamps. These initiators must also be able to form a sufficient quantity of initiating radicals in the lower layers of compositions where radiation is exceedingly low. Surprisingly, the special bisacylphosphine oxide initiators used in the novel compositions are particularly suitable in this respect.

The invention is described in more detail by the following Examples in which, and throughout the remainder of the description and in the claims, parts and percentages are by weight, unless otherwise indicated.

EXAMPLE 1

Preparation of bis(2,4,6-trimethylbenzoyl)(2-methylprop-1-yl)phosphine oxide 140.6 ml (0.225 mol; 1.6M) of butyllithium are added dropwise over 30 minutes under nitrogen at 0° C. to a solution of 31.9 ml (0.225 mol) of diisopropylamine in 80 ml of tetrahydrofuran. This solution is added dropwise at −30° C. over 90 minutes to a solution of 41.1 g (0.225 mol) of 2,4,6-trimethylbenzoyl chloride and 12 ml (0.102 mol) of (2-methylprop-1-yl)phosphine in 200 ml of tetrahydrofuran. After stirring for 2 h at −30° C., the yellow solution is warmed to room temperature and washed once with water. The organic phase is dried over magnesium sulfate, filtered, and the filtrate is concentrated on a rotary evaporator. The residue is dissolved in 200 ml of toluene and 11.6 g (0.102 mol) of 30% hydrogen peroxide are added to the solution. The mixture is stirred for 2 h and washed first with water and then with a saturated solution of sodium hydrogencarbonate and afterwards dried over magnesium sulfate and filtered. The solution is concentrated on a rotary evaporator. Crystallisation of the residue from hexane gives 27.8 g (68.5% of theory) of the above compound as a yellow powder with a melting point of 85°–86 °C.

| Elemental analysis: | | | |
|---|---|---|---|
| calcd % C | 72.34 | found % C | 72.13 |
| found % H | 7.84 | found % H | 7.94 |

EXAMPLES 2–10

The compounds of Examples 2–10 are prepared in general accordance with the procedure described for the preparation of the compound of Example I. The compounds and the analytical data are set forth in Table 1.

TABLE 1

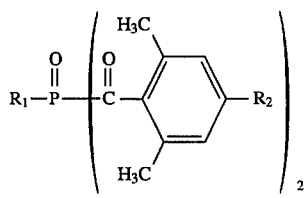

| | | | Melting | Elem. analysis clcd [%] found | |
|---|---|---|---|---|---|
| Ex. | $R_1$ | $R_2$ | point [°C.] | C | H |
| 2 | n-$C_4H_9$ | $CH_3$ | 58 | 72.34 | 7.84 |
| | | | | 72.08 | 8.01 |
| 3 | $CH(CH_3)C_2H_5$ | $CH_3$ | 115 | 72.34 | 7.84 |
| | | | | 72.23 | 7.93 |
| 4 | $C(CH_3)_3$ | $CH_3$ | 160 | 72.34 | 7.84 |
| | | | | 72.21 | 8.06 |
| 5 | cyclohexyl | $CH_3$ | 140 | 73.56 | 7.4 |
| | | | | 73.39 | 8.06 |
| 6 | n-$C_8H_{17}$ | $CH_3$ | oil | 73,98 | 8.65 |
| | | | | 73.83 | 8.89 |
| 7 | $CH_2CH(CH_3)CH_2C(CH_3)_3$ | $CH_3$ | resin | 73.98 | 8.65 |
| | | | | 73.97 | 8.98 |
| 8 | $CH_2CH(CH_3)_2$ | H | 54 | 71.33 | 7.35 |
| | | | | 71.32 | 7.54 |
| 9 | $CH_2CH(CH_3)CH_2C(CH_3)_3$ | H | resin | 73.21 | 8.27 |
| | | | | 73.15 | 8.47 |
| 10 | phenyl | $CH_3$ | 128–129 | 74.63 | 6.50 |
| | | | | 74.53 | 6.65 |

EXAMPLE 11

Cure of a clear varnish formulation

A formulation is prepared from

| | |
|---|---|
| 93.0 parts | of polyester acrylate (® Ebecryl 830, UCB, Belgium) |
| 4.5 parts | of 1,6-hexanediol diacrylate |
| 2.5 parts | of trimethylolpropane triacrylate |
| 4.0 parts | of bis(2,4,6-trimethylbenzoyl)-(2-methylprop-1-yl)phosphine oxide |

A coating on wood is applied with a 100 µm split doctor blade. The coating is exposed to direct sunlight (Basel, August 1991). The wipe resistance of the cured coating is tested by rubbing a paper tissue over the surface. The coating is wipe-resistant after exposure to sunlight for 10 minutes. The wipe-resistant coating is further kept in sunlight and the increase in hardness is monitored by determined pendulum hardness according to König (DIN 53 157) The values are reported in the following Table 2.

TABLE 2

| Duration of cure [min] | Pendulum hardness [s] |
|---|---|
| 15 | 124 |
| 25 | 147 |
| 35 | 157 |
| 65 | 173 |
| 125 | 176 |
| 395 | 182 |

EXAMPLE 12

Cure of a clear varnish formulation

A formulation is prepared in accordance with Example 11, applied to wood and cured, but replacing bis(2,4,6-trimethylbenzoyl)-(2-methylprop-1-yl)phosphine oxide with bis(2,4,6-trimethylbenzoyl)phenylphosphine oxide. The coating is wipe-resistant after exposure to sunlight for 10 minutes and has a pendulum hardness of 115 s.

EXAMPLE 13

Cure of a white enamel formulation

A formulation is prepared from

| | |
|---|---|
| 72.5 parts | of unsaturated polyester/styrene ® Roskydal 502 (Bayer, Germany) |
| 25.0 parts | of rutile-titanium dioxide R-Tc2 (Tioxide, France) |
| 0.5 part | of flow control agent ® Byk 300 (Byk-Mallinckrodt) |
| 2.0 parts | of bis(2,4,6-trimethylbenzoyl)phenylphosphine oxide |

Coats are applied with a 150 µm split doctor blade to chipboards provided with a light undercoat and exposed to sunlight. After 30 minutes the surface is tack-free and the pendulum hardness is 42 s. After a 1 h postcure the pendulum hardness is 111 s.

EXAMPLE 14

Cure of a moulded object made from a composite

A formulation is prepared from

| | |
|---|---|
| 98.0 parts | of unsaturated polyester/styrene Roskydal 500A (Bayer, Germany) |
| 1.5 parts | of 1-benzoyl-1-hydroxy-1-methylethane) ® Darocur 1173 (Ciba, Switzerland |
| 0.5 part | of bis(2,4,6-trimethylbenzoyl)(2-methyl-prop-1- |

0.5 pan of bis(2,4,6-trimethylbenzoyl)(2-methyl-prop-1-yl)phosphine oxide A loosely woven glass cloth as matrix material is fitted into a pipe mould having a diameter of 9 cm and impregnated with the formulation. The weight ratio of glass cloth to formulation is 1:2. A precure takes place after exposure to sunlight for 5 minutes. The cured pan is removed from the mould and further cured in sunlight. A moulded part with high mechanical stability and strength properties is obtained.

EXAMPLE 15

Cure of a clear varnish formulation

A formulation is prepared from

| | |
|---|---|
| 93.0 parts | of polyester acrylate (® Ebecryl 830, UCB, Belgium) |
| 4.5 parts | of 1,6-hexanediol diacrylate |
| 2.5 parts | of trimethylolpropane triacrylate |
| 4.0 parts | of photoinitiator |

The photoinitiator used in one test series is bis(2,4,6-trimethylbenzoyl)cyclohexylphosphine oxide and bis(2,4,6-trimethylbenzoyl)-(2,4,4-trimethylpentyl)phosphine oxide in a second test series. A coating is applied to cardboard with a 6 μm split doctor blade and exposed to direct sunlight. The wipe-resistance of the cured coating is tested by rubbing the surface with a paper tissue. Both coatings are wipe-resistant after exposure to sunlight for 15 minutes.

EXAMPLE 16

Cure of a clear varnish formulation

A formulation is prepared in accordance with Example 11, using as photoinitiator 4 parts of each of bis(2,4,6-trimethylbenzoyl)-(2-methylprop-1-yl)phosphine oxide and bis(2,4,6-trimethylbenzoyl)phenylphosphine oxide. Chipboards are coated with these formulations using a 100 μm split doctor blade. The coatings are cured with 5 TL 03 lamps (Philips) at a distance of 15 cm. Both coatings are cured tack-free after exposure for 8 minutes.

EXAMPLE 17

Cure of a white enamel formulation

Formulations are prepared from

| | |
|---|---|
| 72.5 parts | of unsaturated polyester/styrene ® Roskydal 502 (Bayer, Germany) |
| 25.0 parts | of rutile-titanium dioxide R-Tc2 (Tioxide, France) |
| 0.5 part | of flow control agent ® Byk 300 (Byk-Mallinckrodt) |
| 2.0 parts | of photoinitiator |

Chipboards are coated with these formulations using a 150 μm split doctor blade. The coatings are cured with 5 TL 03 lamps (Philips). The time after which the coatings are tack-free is determined. The photoinitiators used and the results obtained are indicated in Table 3.

TABLE 3

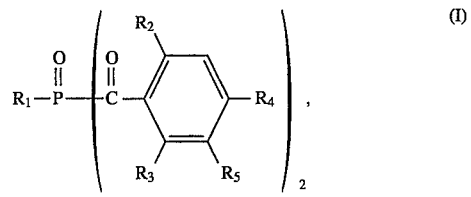

| Photoinitiator | | | | Tack-free after |
|---|---|---|---|---|
| $R_{11}$ | $R_{12}$ | $R_{13}$ | $R_{14}$ | [min] |
| $CH_3$ | $CH_3$ | $CH_3$ | 2-methylprop-1-yl | 3 |
| $CH_3$ | $CH_3$ | $CH_3$ | phenyl | 3 |
| $CH_3$ | H | $CH_3$ | 2-methylprop-1-yl | 10 |

What is claimed is:

1. A process for curing ethylenically unsaturated polymerisable compounds, which comprises adding to said compounds at least one photoinitiator of formula I $$\left( R_1-\overset{O}{\underset{\|}{P}}-\overset{O}{\underset{\|}{C}}-\begin{array}{c}R_2\\ \diagup\\ \diagdown\\ R_3\end{array}-\begin{array}{c}\\ R_4\\ R_5\end{array}\right)_2 \quad (I)$$

wherein
$R_1$ is $C_1$–$C_{12}$alkyl, cyclopentyl, cyclohexyl, unsubstituted phenyl, naphthyl or biphenyl,
$R_2$ and $R_3$ are each independently of the other $C_1$–$C_{12}$alkyl,
$R_4$ is hydrogen or $C_1$–$C_{12}$alkyl, and
$R_5$ is hydrogen or methyl,
and irradiating the mixture so obtained with daylight or with light sources equivalent to daylight.

2. A process according to claim 1, wherein $R_1$ in the compound of formula I is $C_2$–$C_{10}$alkyl, cyclopentyl, cyclohexyl or phenyl.

3. A process according to claim 2, wherein $R_1$ in the compound of formula I is $C_3$–$C_8$alkyl, cyclopentyl, cyclohexyl or phenyl.

4. A process according to claim 1, wherein $R_1$ in the compound of formula I is $C_4$–$C_{12}$alkyl, cyclopentyl or cyclohexyl, $R_2$ and $R_3$ are each independently of the other $C_1$–$C_{12}$alkyl and $R_4$ is hydrogen or $C_1$–$C_{12}$alkyl.

5. A process according to claim 1, wherein $R_2$ and $R_3$ in the compound of formula I are $C_1$–$C_4$alkyl and $R_4$ is hydrogen or $C_1$–$C_4$alkyl.

6. A process according to claim 5, wherein $R_2$, $R_3$ and $R_4$ in the compound of formula I are methyl and $R_5$ is hydrogen.

7. A process according to claim 1, wherein $R_1$ in the compound of formula I is $C_3$–$C_8$alkyl.

8. A process according to claim 7, wherein $R_1$ in the compound of formula I is isobutyl.

9. A process according to claim 1, wherein $R_1$ in the compound of formula I is phenyl.

10. A process according to claim 1, wherein the ethylenically unsaturated polymerisable compounds are a mixture of (i) at least one oligomeric compound and (ii) at least one monomer.

11. A process according to claim 10, wherein the ethylenically unsaturated polymerisable compounds are a mixture of (i) unsaturated polyesters and (ii) acrylates, methacrylates and/or styrene.

12. A process according to claim 11, wherein the ethylenically unsaturated polymerisable compounds are a mixture of (i) unsaturated polyesters and (ii) acrylates and/or methacrylates.

13. A process according to claim 11, wherein the unsaturated polyesters (i) are prepared from maleic acid, fumaric acid and/or phthalic acid and one or more than one diol, and have molecular weights of 500 to 3000.

14. A process according to claim 10, wherein the ethylenically unsaturated polymerisable compounds are a mixture of (i) polyester acrylates and (ii) acrylates and/or methacrylates.

15. A process according to claim 1, wherein the ethylenically unsaturated polymerisable compounds are dissolved or emulsified in water.

16. A process according to claim 1, wherein the photoinitiator is used in an amount of 0.05 to 15% by weight, preferably 0.2 to 5% by weight.

17. A process according to claim 1, wherein other photoinitiators and/or other additives are used in addition to the photoinitiator of formula (I).

18. A composition comprising (A) at least one ethylenically unsaturated polymerisable compound, and (B) at least one photoinitiatior of formula I, which composition is curable by irradiation with daylight or with light sources equivalent to daylight.

19. A process for coating surfaces, which comprises applying a composition as claimed in claim 18 to said surface and curing the layer by irradiation with daylight or with light sources equivalent to daylight.

* * * * *